United States Patent [19]

Kojima et al.

[11] 4,326,062

[45] Apr. 20, 1982

[54] MANUFACTURE OF POLYMERIZED 2,2,4-TRIMETHYL-1,2-DIHYDROQUINOLINE

[75] Inventors: Takashi Kojima, Toyonaka; Eizo Okino, Nishinomiya; Ryozo Ishimoto, Toyonaka, all of Japan

[73] Assignee: Sumitomo Chemical Company, Ltd., Osaka, Japan

[21] Appl. No.: 171,239

[22] Filed: Jul. 22, 1980

[30] Foreign Application Priority Data

Jul. 26, 1979 [JP] Japan ................... 54/95824

[51] Int. Cl.³ ............................. C07D 215/06
[52] U.S. Cl. .................... 546/166; 546/165; 546/181; 260/800; 524/86
[58] Field of Search .............. 546/165, 166, 181

[56] References Cited

U.S. PATENT DOCUMENTS 4,158,000  6/1979  Nagasaki et al. .......... 260/45.8 NW

FOREIGN PATENT DOCUMENTS 943962  3/1974  Canada ........................ 546/181
2832126  2/1979  United Kingdom .............. 546/165

OTHER PUBLICATIONS

Craig, J. Am. Chem. Soc., vol. 60, pp. 1458–1465 (1938).
Elliott, Jr., et al., Tetrahedron, vol. 19, pp. 833–838 (1963).

*Primary Examiner*—Donald G. Daus
*Assistant Examiner*—Diana G. Rivers
*Attorney, Agent, or Firm*—Wenderoth, Lind & Ponack

[57] ABSTRACT

2,2,4-Trimethyl-1,2-dihydroquinoline polymer containing 25% by weight or more of the dimer is effectively prepared by the polymerization of 2,2,4-trimethyl-1,2-dihydroquinoline monomer in the presence of hydrochloric acid, the concentration of hydrochloric acid being from 15 to 25% by weight, and the amount of hydrochloric acid being 0.2 to 0.5 mole per mole of the total of the monomer and impurity amines contained in the monomer. The polymer is useful as an antioxidant for rubber.

4 Claims, No Drawings

MANUFACTURE OF POLYMERIZED 2,2,4-TRIMETHYL-1,2-DIHYDROQUINOLINE

The present invention relates to a method for producing polymerized 2,2,4-trimethyl-1,2-dihydroquinoline (hereinafter referred to as RD polymer) useful as an antioxidant for rubber, particularly RD polymer containing not less than 25% of dimerized 2,2,4-trimethyl-1,2-dihydroquinoline (hereinafter referred to as RD dimer, and 2,2,4-trimethyl-1,2-dihydroquinoline is referred to as RD monomer).

It is well known that RD polymer is an excellent antioxidant for rubber, and particularly RD polymer containing a large amount of RD dimer has exhibited markedly superior performance (Published Unexamined Japanese Patent Application No. 145854/1978).

There are many well-known methods for the polymerization of RD monomer, for example a method using anhydrous aluminum chloride as catalyst, and one using conc. hydrochloric acid. In the former case, however, a trace amount of water present in the reaction system largely affects the progress of the polymerization, and therefore, this method is not suitable for the commercial production of the objective RD polymer containing a large amount of RD dimer, because it is too difficult to control the reaction. In the latter case, the viscosity of the reaction system increases with the progress of the polymerization, and the stirring of the system becomes too difficult for the reaction to proceed further.

In order to overcome the drawback of this latter case, the inventors made an attempt to lower the viscosity of the reaction system by adding a solvent such as toluene to the system. But the viscosity of the system increased also during the reaction, and the polymer having a desired composition was not obtained.

The inventors proposed a method for producing RD monomer by reacting aniline with acetone (or diacetone alcohol or mesityl oxide) at not more than 120° C. using p-toluenesulfonic acid as catalyst (Japanese Published Unexamined Patent Application No. 40661/1980). This reaction product (crude RD monomer) contains about 20 to 40% of unreacted aniline, and when it is used as a material for polymerization according to the conventional method using conc. hydrochloric acid, the reaction itself will be continued by raising the reaction temperature to not less than 130° C. to decrease the viscosity of the reaction system. But, an adduct between RD monomer and aniline, 4-(p-anilino)-2,2,4-trimethyl-1,2,3,4-tetrahydroquinoline, represented by the formula (I),

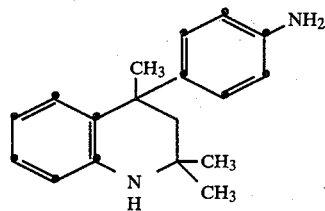

is produced in large amounts as by-product, markedly lowering the performances of RD polymer as an antioxidant.

For the reasons described above, the inventors extensively studied to develop a method for producing RD polymer containing a large amount of RD dimer in a commercially advantageous manner and at a low cost. As a result, it was found that such the polymer can easily be obtained by polymerizing RD monomer in a medium comprising a specified amount of hydrochloric acid of a specified concentration (without a difficulty such that the viscosity of the reaction system increases).

The present invention provides a method for producing polymerized 2,2,4-trimethyl-1,2-dihydroquinoline containing 25% by weight or more of dimerized, 2,2,4-trimethyl-1,2-dihydroquinoline, which comprises subjecting a raw 2,2,4-trimethyl-1,2-dihydroquinoline monomer to polymerization in the presence of hydrochloric acid, the concentration of hydrochloric acid being from 15 to 25% by weight, and the amount of hydrochloric acid being from 0.2 to 0.5 mole per mole of the total of 2,2,4-trimethyl-1,2-dihydroquinoline and impurity amines contained in the monomer.

The raw RD monomer usable in the present invention need not always be of high purity, and includes those which are obtainable by the reaction between aniline and acetone, diacetone alcohol or mesityl oxide in a conventional manner including the manner as disclosed in the aforesaid Japanese Published Unexamined Patent Application No. 40661/1980, and which may contain impurities such as unreacted aniline and by-produced high boiling amines. Thus, there are usually used as the raw RD monomer the reaction mixture as such obtained by the aforesaid reaction, and the one isolated from the said reaction mixture by purification such as distillation or the like.

The first characteristic of the present invention is that the concentration of hydrochloric acid in the reaction system is from 15 to 25% by weight. When the concentration of the acid is less than 15% by weight, the reaction itself can be advanced, but its rate is too slow to be economical. While concentrations exceeding 25% by weight increase the viscosity of the reaction system to make the control of the reaction difficult.

The second characteristic of the present invention is that the amount of hydrochloric acid is 0.2 to 0.5 mole per mole of the total of RD monomer and the impurity amines contained in the raw RD monomer. When the amount is less than 0.2 mole, the rate of reaction is too slow to be economical. While amounts exceeding 0.5 mole accelerate the rate of polymerization so rapidly that the control of the reaction becomes difficult.

The manner of adding the hydrochloric acid to the reaction system is optional. For example, hydrochloric acid previously adjusted to the specified concentration may be added to the system in the amount as specified above, or the specified amount of hydrochloric acid and water may be separately added to the reaction system so as to adjust the concentration of hydrochloric acid to the concentration as specified above.

The polymerization is carried out at a temperature of 80° to 100° C., preferably 90° to 100° C. under atmospheric pressure. In general, when the temperature exceeds the above temperature range, water in the system is distilled out of the system, so that to keep the specified concentration of hydrochloric acid becomes impossible. While, when the temperature is below the above range, the viscosity of the system is increased to make the control of the reaction difficult. The polymerization is continued under stirring to obtain the desired RD polymer, and can be performed usually within several hours.

After the polymerization is over, the reaction mixture can be subjected to after-treatment in a conventional manner to isolate the desired RD polymer. For example, the reaction mixture is dissolved in an organic solvent (e.g. benzene, toluene, xylene, etc.), followed by neutralization and evaporation of the organic solvent. Alternatively, the reaction mixture is dispersed in water and then treated to be made into granules.

In accordance with the present invention, the desired RD polymer containing a large amount (i.e. 25% or more) of RD dimer having excellent performances as antioxidant, can be produced, irrespective of the quality of the raw RD monomer.

The present invention is illustrated in more detail with reference to the following examples, which are only illustrative, but not limitative, for the scope of the present invention. In the examples, % is by weight.

EXAMPLE 1

To a 500-ml four-necked flask equipped with a thermometer, a stirrer and a condenser were added 87.9%-purity RD monomer (200 g) containing 3.3% of aniline (aniline, 0.07 mole; RD monomer, 1.02 mole; total of the amines, 1.09 mole), conc. hydrochloric acid (41.8 g, 0.41 mole) and water (40 ml). The mixture was heated to 90° C. and kept at 90° to 100° C. for 6 hours with stirring. Thereafter, the reaction solution was diluted with toluene (100 ml), and at 85° to 90° C., it was neutralized with a 45% aqueous sodium hydroxide solution (38.5 g). After allowing to stand still, the solution was separated into aqueous and oily layers, and the aqueous layer was discarded. The oily layer was washed with several 100-ml portions of water.

Toluene was first distilled out of the oily layer, and then 43.5 g of a low-boiling fraction was distilled out at 200° C. and at a reduced pressure of down to 2 mmHg, leaving 146.5 g of RD polymer as residue. This polymer contained 51% of RD dimer and not more than 1% of the aniline/RD monomer adduct.

EXAMPLE 2

To a 500-ml four-necked flask equipped with an acetone-introducing tube, a thermometer, a stirrer and a condenser were added aniline (145.3 g, 1.56 moles) and p-toluenesulfonic acid monohydrate (7.4 g, 0.039 mole), and the mixture was heated to 100° to 120° C. Acetone (906 g) was introduced in 12 hours while keeping the temperature of the reaction system at 100° to 120° C. A crude RD monomer was thus produced.

The composition of the resulting reaction product was as follows: Unreacted aniline, 36.2 g (0.39 mole); RD monomer, 148.7 g (0.86 mole); a high-boiling amine, 44.6 g (0.26 mole); and p-toluenesulfonic acid, 6.7 g. The reaction product was cooled to 95° C., and immediately conc. hydrochloric acid (60 g, 0.59 mole) and water (40 ml) were added, followed by stirring at 95° to 100° C. for 3 hours. After the reaction was finished, the reaction solution was diluted with toluene (100 ml) and neutralized with a 45% aqueous sodium hydroxide solution (59 g). After allowing to stand still, the solution was separated into aqueous and oily layers, and the aqueous layer was discarded. The oily layer was washed with several 100-ml portions of water.

Toluene was first distilled out of the oily layer, and then unreacted aniline and the monomer were distilled out under reduced pressure to obtain 175.5 g of RD polymer. This polymer contained 48% of the dimer and 1.8% of the aniline/monomer adduct.

REFERENCE EXAMPLE 1

In the method of Example 1, only the crude RD monomer (200 g) and conc. hydrochloric acid (41.8 g) were added, and polymerization was carried out at 90° to 100° C. One hour after the beginning of the polymerization, the viscosity of the reaction system began to increase to make uniform stirring very difficult. After 3 hours, a part of the reaction mass was sampled and analyzed, and it was found that the mass contained 47% of the dimer. But, the whole reaction mass in the flask could not be dissolved in toluene (100 ml), making the subsequent treatment impossible.

REFERENCE EXAMPLE 2

In the method of Example 1, the crude RD monomer (200 g), conc. hydrochloric acid (41.8 g) and water (100 ml) were added, the mixture was heated to 90° C. and polymerization was carried out at 90° to 100° C. After 6 hours, it was found that not less than 30% of the monomer was left unreacted. After 14 hours' polymerization, 144.8 g of RD polymer was obtained. This polymer contained 51% of RD dimer.

REFERENCE EXAMPLE 3

In the method of Example 1, the crude RD monomer (200 g), conc. hydrochloric acid (77.3 g, 0.736 mole) and water (74 ml) were added, and the mixture was heated to 90° C. Polymerization was then carefully carried out for 3 hours while keeping the temperature at 91°±1° C. RD polymer thus obtained contained 44% of RD dimer. While when said mixture was heated in the same manner and polymerization was carried out at 95°±1° C. for 2 hours, RD polymer contained 30% of RD dimer, which means that the polymer content increased. Thus, the progress of polymerization is greatly affected even by a slight difference in polymerization temperature, so that it is very difficult to control the composition of RD polymer in an industrial production thereof.

REFERENCE EXAMPLE 4

In the method of Example 1, the crude RD monomer (200 g), conc. hydrochloric acid (11.0 g, 0.1 mole) and water (10.5 ml) were added and heated to 90° C. Polymerization was then carried out at 90° to 100° C. for 18 hours to obtain 145.1 g of RD polymer containing 50% of RD dimer. During the polymerization, the reaction solution was sampled 6 hours after the beginning of the polymerization and analyzed. The result of the analysis showed that 38% of RD monomer was left unreacted.

U.S. Pat. No. 2,718,517 discloses a method for producing RD polymer which comprises polymerizing RD monomer of which about 90% is present as a hydrochloric acid salt. But, this method allowed the polymerization to process too far to obtain the objective RD polymer containing a large amount of RD dimer. This will be shown with reference to the following comparative example.

COMPARATIVE EXAMPLE

In the method of Example 1, the crude RD monomer (200 g), conc. hydrochloric acid (100 g, 0.99 mole) and water (67.0 g) were added (composition of the solution:- water content, about 36%; ratio of RD monomer hydrochloride to free RD monomer, about 9:1). The mixture was heated to 95° C., and polymerization was carefully carried out at 95° to 96° C. for 9 hours to obtain 162.6 g of RD polymer. The polymer had an extremely high polymer content and the RD dimer content of the polymer was only 6%.

What is claimed is:

1. A method for producing polymerized 2,2,4-trimethyl-1,2-dihydroquinoline containing 25% by weight or more of dimerized 2,2,4-trimethyl-1,2-dihydroquinoline, which comprises subjecting a raw 2,2,4-trimethyl-1,2-dihydroquinoline monomer to polymerization in the presence of hydrochloric acid, the concentration of hydrochloric acid being from 15 to 25% by weight, and the amount of hydrochloric acid being from 0.2 to 0.5 mole per mole of the total of 2,2,4-trimethyl-1,2-dihydroquinoline and impurity amines contained in the monomer.

2. The method according to claim 1, wherein the polymerization is carried out at a temperature of 80° to 100° C.

3. The method according to claim 1, wherein the raw monomer is obtained by the reaction of aniline with acetone, diacetone alcohol or mesityl oxide at a temperature of not higher than 120° C. using p-toluenesulfonic acid as a catalyst, followed by purification.

4. The method according to claim 1, wherein the raw monomer is a reaction mixture obtained by the reaction of aniline with acetone, diacetone alcohol or mesityl oxide at a temperature of not higher than 120° C. using p-toluenesulfonic acid as a catalyst.

* * * * *